(12) United States Patent
Tumlinson (10) Patent No.: US 9,895,057 B2
(45) Date of Patent: Feb. 20, 2018

(54) FUNCTIONAL VISION TESTING USING LIGHT FIELD DISPLAYS

(71) Applicant: Carl Zeiss Meditec, Inc., Dublin, CA (US)

(72) Inventor: Alexandre R. Tumlinson, San Leandro, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/120,063

(22) PCT Filed: Apr. 20, 2015

(86) PCT No.: PCT/EP2015/058529
§ 371 (c)(1),
(2) Date: Aug. 18, 2016

(87) PCT Pub. No.: WO2015/162098
PCT Pub. Date: Oct. 29, 2015

(65) Prior Publication Data
US 2017/0055825 A1     Mar. 2, 2017

Related U.S. Application Data

(60) Provisional application No. 61/983,777, filed on Apr. 24, 2014.

(51) Int. Cl.
*A61B 3/02*     (2006.01)
*A61B 3/10*     (2006.01)
(Continued)

(52) U.S. Cl.
CPC ............ *A61B 3/024* (2013.01); *A61B 3/0008* (2013.01); *A61B 3/0025* (2013.01);
(Continued)

(58) Field of Classification Search
CPC .. A61B 3/00; A61B 3/103; A61B 3/02; A61B 3/113; A61B 3/1015; A61B 3/1225;
(Continued)

(56) References Cited

U.S. PATENT DOCUMENTS 3,855,417 A    12/1974  Fuller
4,998,818 A     3/1991  Kugler et al.
(Continued)

FOREIGN PATENT DOCUMENTS

EP    1983318 A1    10/2008
EP    2468174 A1     6/2012
(Continued)

OTHER PUBLICATIONS

Canon Inc., "Canon Successfully Develops World's First APS-H-Size CMOS Image Sensor to Realize Record-High Resolution of 120 Megapixels", News Releases, online available at <www.canon.com/news/2010/aug24e.html>, Aug. 24, 2010, 2 pages.
(Continued)

*Primary Examiner* — Dawayne A Pinkney
(74) *Attorney, Agent, or Firm* — Morrison & Foerster LLP (57) ABSTRACT

Systems and methods for performing visual field testing using light field displays are described. The light field display (201, 202; 801; 504; 601-604; 704; 801), that can correct for the focus and cylindrical refractive error of the subject, can be used to perform a variety of visual field testing strategies by rendering visual stimuli to the eye (203). The light field display may be included near the subject's eye, or reimaged by a relay optical system (802). Several embodiments of head and arm mounted systems (711; 704) including a near eye light field display (704) are presented.

22 Claims, 6 Drawing Sheets

(51) Int. Cl.
*A61B 3/14* (2006.01)
*A61B 3/00* (2006.01)
*A61B 3/024* (2006.01)
*A61B 3/032* (2006.01)

(52) U.S. Cl.
CPC .......... *A61B 3/0041* (2013.01); *A61B 3/0075* (2013.01); *A61B 3/032* (2013.01)

(58) Field of Classification Search
CPC .......... A61B 3/111; A61B 3/08; A61B 3/0285; A61B 3/1208; A61B 3/032; A61B 3/024; G02C 13/005
USPC ....... 351/200, 202, 205, 221–226, 246, 210, 351/204, 201, 209, 211, 218
See application file for complete search history.

(56) References Cited

U.S. PATENT DOCUMENTS

| | | |
|---|---|---|
| 5,177,511 A | 1/1993 | Feuerstein et al. |
| 5,220,361 A | 6/1993 | Lehmer et al. |
| 5,323,194 A | 6/1994 | Campbell et al. |
| 5,737,060 A | 4/1998 | Kasha, Jr. |
| 5,864,384 A | 1/1999 | McClure et al. |
| 5,880,812 A | 3/1999 | Solomon |
| 6,065,837 A | 5/2000 | Goldfain et al. |
| 6,386,706 B1 | 5/2002 | McClure et al. |
| 6,486,943 B1 | 11/2002 | Burns et al. |
| 6,529,331 B2 | 3/2003 | Massof et al. |
| 7,364,295 B2 | 4/2008 | Tawada |
| 7,780,364 B2 | 8/2010 | Raskar et al. |
| 7,936,392 B2 | 5/2011 | Ng et al. |
| 8,132,916 B2 | 3/2012 | Johansson |
| 8,243,157 B2 | 8/2012 | Ng et al. |
| 8,471,897 B2 | 6/2013 | Rodriguez Ramos et al. |
| 8,668,338 B2 | 3/2014 | Johansson et al. |
| 8,684,529 B2 | 4/2014 | Johansson et al. |
| 2004/0160576 A1 | 8/2004 | Lai et al. |
| 2009/0273843 A1 | 11/2009 | Raskar et al. |
| 2011/0299034 A1* | 12/2011 | Walsh ................... A61B 3/102 351/206 |
| 2013/0169934 A1 | 7/2013 | Verdooner |
| 2014/0306866 A1* | 10/2014 | Miller .................. G06T 19/006 345/8 |

FOREIGN PATENT DOCUMENTS

| | | |
|---|---|---|
| WO | 2010/045564 A2 | 4/2010 |
| WO | 2014/140849 A2 | 9/2014 |

OTHER PUBLICATIONS

Dehoog et al., "Fundus Camera Systems: A Comparative Analysis", Applied Optics, vol. 48, No. 2, Jan. 10, 2009, pp. 221-228.
Georgiev et al., "Focused Plenoptic Camera and Rendering", Journal of Electronic Imaging, vol. 19, No. 2, Apr.-Jun. 2010, pp. 021106-1-021106-11.
International Preliminary Report on Patentability received for PCT Patent Application No. PCT/EP2012/063192, dated Jan. 23, 2014, 9 pages.
International Preliminary Report on Patentability received for PCT Patent Application No. PCT/EP2015/058529, dated Nov. 3, 2016, 10 pages.
International Search Report and Written Opinion received for PCT Patent Application No. PCT/EP2012/063192, dated Sep. 19, 2012, 12 pages.
International Search Report and Written Opinion received for PCT Patent Application No. PCT/EP2015/058529, dated Jun. 29, 2015, 14 pages.
Lanman et al., "Near-Eye Light Field Displays", ACM Transactions on Graphics, vol. 32, No. 6, Nov. 2013, 10 pages.
Lumsdaine et al., "The Focused Plenoptic Camera", IEEE, 2009, 8 pages.
Ng et al., "Light Field Photography with a Hand-held Plenoptic Camera", Stanford Tech Report CTSR, 2005, pp. 1-11.
Ng, Ren, "Digital Light Field Photography", Doctoral Dissertation, Stanford University, Jul. 2006, 203 pages.
Non-Final Office Action received for U.S. Appl. No. 13/542,516, dated Jun. 11, 2014, 5 pages.
Notice of Allowance received for U.S. Appl. No. 13/542,516, dated Dec. 8, 2014, 7 pages.
Perwass et al., "The Next Generation of Photography: An Introduction to Light Field Photography", Raytrix GmbH, available online at <http://www.raytrix.de/index.php/Technology.html>, Jan. 2010, 33 pages.
Raskar et al., "Glare Aware Photography: 4D Ray Sampling for Reducing Glare Effects of Camera Lenses", ACM Transactions on Graphics, vol. 27, No. 3, Aug. 2008, pp. 56:1-56:10.
Tokuda et al., "Holocamera for 3-D Micrography of the Alert Human Eye", Applied Optics, vol. 19, No. 13, Jul. 1, 1980, pp. 2219-2225.

\* cited by examiner

Stimulus size:

| Stimulus (Goldmann) | Angle [degrees] |
|---|---|
| I | 0.11 |
| II | 0.22 |
| III | 0.43 |
| IV | 0.86 |
| V | 1.72 |

FUNCTIONAL VISION TESTING USING LIGHT FIELD DISPLAYS

CROSS-REFERENCE TO RELATED APPLICATIONS

This application is a National Phase application under 35 U.S.C. § 371 of International Application No. PCT/EP2015/058529, filed Apr. 20, 2015, which claims priority to U.S. Provisional Patent Application No. 61/983,777, filed Apr. 24, 2014, the disclosure of each of which is hereby incorporated herein by reference in its entirety.

TECHNICAL FIELD

One or more embodiments of the present application relate generally to a method and apparatus for performing a visual field test. In particular, one or more embodiments disclose methods and apparatuses for controlling the displayed images for use in visual field testing.

BACKGROUND

Visual Field Testing

The gold standard in visual field analysis has been marketed for some time by the assignee herein under the trademark Humphrey® Field Analyzer (HFA). The HFA projects a light stimulus on an aspheric bowl (see for example U.S. Pat. No. 5,323,194). The HFA test image is intuitively quite simple. The HFA presents stimulus targets of various sizes and intensities on a background of fixed, uniform intensity, and determines whether the subject perceived the stimuli. For example, one HFA stimulus is a white circle of diameter 0.43 degrees presented against a background with a brightness of 31.5 apostilbs for a duration of 200 ms. The stimulus brightness is one of 52 precisely defined intensities and it is presented at a location relative to a fixed position. Nominally, the fixed position is defined relative to a fixation target, on which the subject fixates their gaze. The stimulus may be repeated a different location across the field of view. The full field of view included by HFA is as large as +/−90 degrees in the horizontal axis, while the most diagnostically relevant regions sufficient for most care decisions are within the central +/−30 degrees. The subject informs the device if the stimulus is perceived by pressing a button. The gaze of the patient may be monitored and analyzed throughout the test using various methods including but not limited to corneal reflexes and images (see for example U.S. Pat. Nos. 5,220,361 and 8,684,529 hereby incorporated by reference)

In order to visualize the stimulus on the bowl, the refractive error of the subject should be corrected to allow focus on the surface of the bowl, particularly when performing test in the central 30 degree field. This is done so that the image of the stimulus projected onto the retina by the optics of the eye is functionally equivalent, primarily in terms of intensity and size, between an emmetropic individual who requires no refractive correction for clear focus, and myopes, hyperopes, and those with astigmatism who require refractive correction to focus clearly. This allows the data to be clearly placed in context and allows the clinician to make calibrated treatment decisions, understanding how a subject's vision deficits will affect daily life over the course of their probable lifetime. The HFA includes a holder in which to place a trial lens matching the patients refractive correction. Two slots on the holder allow manual addition of spherical lens and a cylindrical lens. A potential upgrade to HFA adds a lens (e.g. an Alvarez lens) with continuously adjustable optical power to correct refractive errors from approximately −10 to +10 Diopters by means of an electrically controllable moving part (see for example U.S. Pat. No. 8,668,338). The Alvarez lens does not however manage cylindrical power, so operators are recommended to use the trial lens setup with patients who have significant astigmatism. The operator typically records the lens power (and orientation in the case of astigmatism) to aid in the setup for the next exam. When testing outside the central 30 degree field the operator should remove any trial lens to allow an unobstructed view.

The bowl of the HFA necessitates that the perimeter have a large volume. It is desirable to reduce the office footprint of a desktop device in clinical practice. A large device generally requires that the subject move to the device, and conform their posture to the fixed position of the immobile device. The patients who require visual testing are most frequently elderly, and are frequently afflicted with comorbidities. Unnecessary movements around the clinic are both physically challenging for the patient and time consuming for the medical practice. Visual field testing may take several minutes. Attempting to maintain a precisely defined posture for an extended time becomes difficult or impossible for some subjects bent away from the average by age or disease. The effort involved to move between multiple stations within a practice, or maintain a painful posture requires concentration which can degrade testing performance. The HFA is generally a single purpose device. When a patient requires other tests, he she moves to a different location to receive those tests. Visual field tests may be performed binocularly or monocularly. In the more frequent monocular test, the unused eye is typical covered by an eye patch to prevent stimulus.

Several alternative technologies for visual field analysis have been developed. One such technology also marketed by the assignee herein under the trademarks Humphrey FDT® perimeter and Humphrey Matrix® perimeter utilizes a frequency doubling illusion target stimulus created by a video monitor, while a lens near the eye magnifies the display to cover a large portion of the diagnostically relevant field of view. Several groups have proposed head mounted perimeters. (see, for example U.S. Pat. Nos. 5,737,060, 5,864,384, and 5,880,812). To date no head mounted device has achieved clinical acceptance. It is desirable that any head mounted device be light enough that it may be comfortably worn by an elderly patient for an extended period of time.

Light Field Displays

As described by Ren Ng, the "light field" is a concept that includes both the position and direction of light propagating in space (see for example U.S. Pat. No. 7,936,392). The idea is familiar from the ray representation of light. We know that light energy is conserved as it passes along straight line paths through space. The light energy can be represented in a 4 dimensional space $L(u,v,s,t)$ with an intensity value at each of $(u,v)$ positions within a plane, and at angular rotations $(s,t)$ about each of those axes. The concept is used extensively in computer graphics simulations. With the information from a light field, the rays can be propagated to destinations in other planes. The process of computing the light intensity at another plane and presenting it as if it were imaged on a virtual film is also called reconstruction. The methods described by U.S. Pat. No. 7,936,392 B2, as well as the doctoral thesis by the same author (R. Ng, "Digital light field photography" 2006) are exemplary descriptions of light field sensor technology, the mathematics for propagation of the light fields, and the practice of image reconstruction techniques using light fields, both of which are hereby incorporated by reference. Within computer graphics simulations it is also common to accurately render ray paths of light through refracting surfaces based upon a model of the space through which rays travel. Upon interacting with a refracting surface the angle of a ray of light is changed according to Snell's Law; after changing direction the ray again propagates in a straight line towards the destination plane.

Figure 1:
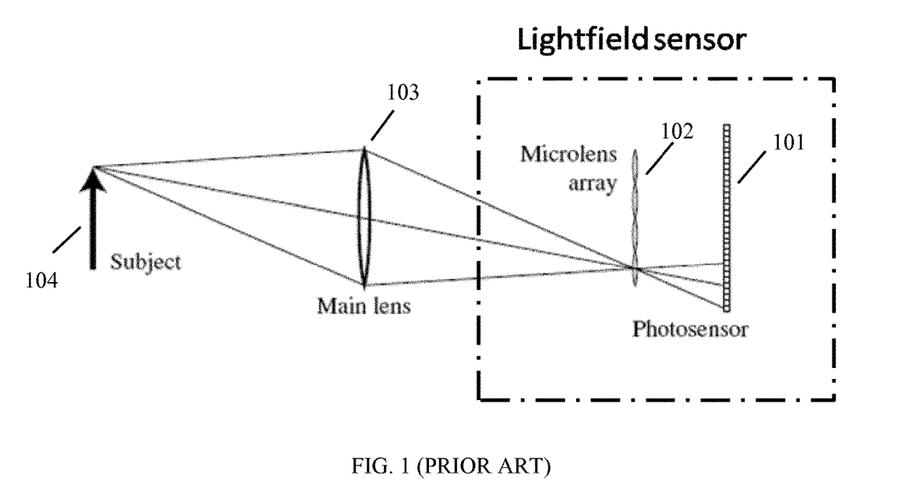
FIG. 1 illustrates the basic components of a light field sensor as described in the prior art.

A light field sensor for use in a digital focus camera is achieved by placing a sensor array 101 at or near the back focal plane of a microlens array (lenticular array) 102 as illustrated in FIG. 1. This light field sensor is placed in a supporting assembly containing other optical components such as a main lens 103 to shape and constrain the light from the subject 104 to best fit the light field sensor geometry. In this way a ray is constrained in position by the individual lens in the array (lenslet) through which it passed, and in angle by the specific sensor pixel it is incident upon behind the lenticular array. Light field sensors may be created by other means known currently or by other methods which are likely to be devised in the future. One such alternative light field sensor may use an array of pinholes instead of a lenticular array. Another alternative may place the sensor array at a distance significantly different from the back focal plane of the lenticular array (Lumsdaine et al. "The Focused Plenoptic Camera", ICCP April 2009). Such variations may achieve advantages in angular or spatial resolution given a particular sensor or lenticular array spacing. Ren Ng describes properties of generalized light field sensors in his dissertation work which extend beyond the format of the simple lenticular array placed in front of a sensor array. It is to be understood that all such representations are included if we speak of a lens array as one such representation of a light field sensor.

A light field display incorporates similar concepts, however rather than detecting the light rays, the display creates them. Douglas Lanman describes how a virtual image of a wide field scene may be created by a light field display consisting of a high pixel density organic light emitting diode (OLED) array, and a lenslet array (Douglas Lanman et al. "Near-Eye Light Field Displays", in ACM SIGGRAPH 2013 Emerging Technologies, July 2013). He makes application of this technology to create a very compact, lightweight head mounted display, especially for the representation of 3D environments for entertainment and other purposes. The OLED display is located at the back focal plane of the lenslet array. Approximately underneath each lenslet, a small portion of a larger scene (partial image) is rendered by the OLED array. When the array is placed near the human eye, the pupil of the eye selects a small subset of the rays emitted by the display. The scene observed by the human eye though each lenslet makes up a small portion of a larger scene composed of the scenes transmitted through all of the lenslets. When the eye is aligned correctly relative to the display, and the images rendered correctly on the OLED display, a consistent widefield image is composed from the partial images.

Each lenslet has a small aperture compared to the eye, and therefore it's scene has a large depth of field. That is, the partial image from each lenslet is relatively insensitive to focus errors. The scenes observed by the human eye through neighboring lenslets have a large degree of overlap. To the extent that corresponding pixels in neighboring scenes overlap at the retina, the scene appears to be in focus. That is, the same scene is projected on the retina, but from different angles, corresponding to different locations within the pupil. A focus error by the eye causes a lateral shift of images on the retina, when the light travels off center through the pupil, thus blurring the superposition of partial images. By changing the relationship between the overlapping scenes digitally, a computer rendering can simulate a change in 'focus.'

The scene can be described as the super position of views of a scene from different angles, or using the notation familiar to light fields in general, the light energy can be represented in a 4 dimensional space $L(u,v,s,t)$ with an intensity value at each of $(u,v)$ positions within a plane, and at angular rotations $(s,t)$ about each of those axes. In a display the intensity value is set for each coordinate by turning on the associated source display pixel at the appropriate intensity. After propagating the light field to the image sensing retina of the eye, we consider a lateral retina position $(u,v)$; illuminated from angle (i.e. pupil location) coordinates $(s,t)$. The summation of all angular channels at a position gives the integrated intensity at a position in the retinal plane $Ir(u,v)$.

SUMMARY

The present application is directed towards systems and methods for performing visual field analysis using one or more light field displays. Such a device would comprise: a light field display for generating visual stimuli for presentation to the eye, a means to record the response of the subject to the visual stimulus, and a processor for analyzing the responses to determine the eye's visual sensitivity. The rendering of the light field display is adjusted to correct for common refractive errors including spherical and cylindrical error. The light field may be used to present simple, isolated stimuli with relatively low spatial resolution, and precisely controlled brightness, mimicking the test strategy of the HFA or to present other functional vision testing schemes. The brightness of stimuli 'focused' on the retina may be controlled to a factor smaller than the bit depth associated with any pixel in the source array by dithering the brightness of the individual pixels which are superimposed to create the 'focused' stimuli. The light field may also be presented in a 'foveated' manner presenting the highest spatial resolution in the location of central vision. Eye tracking provided in the device can aid with rendering the stimulus, and additionally provides information useful to the exam. Tests may be performed in either a binocular or monocular manner controlling which display pixels are activated. The light field display may be presented in multiple panels to achieve a wide field of view. The wrap around effect created by multiple panels can aid to control the visual ambient environment. This control may be further assisted by non-light field projecting wraparound panels with a controlled homogeneous luminance Recording of the subject's response may be accomplished in a variety of ways including but not limited to a hand controller or voice activation. The system may be used to deliver other types of stimulus to perform other visual function tests including alternate visual field strategies such as frequency doubling stimulus, visual acuity tests (Snellen chart), stereopsis tests etc.

The light field display may be included near the subject's eye, or reimaged by a relay optical system. A system including a near eye display may be head mounted. A head mounted display system may include an outward facing camera which optionally provides a view of the outside world into the goggles to facilitate communication with an operator. Alternative embodiments where the device is held within a fixed distance of the patient without head mounting are also considered.

BRIEF DESCRIPTION OF THE DRAWINGS

FIG. 7(b) illustrates an arm mounted display embodiment.

FIG. 7(c) illustrates a head mounted display embodiment.

DETAILED DESCRIPTION

In visual field testing also commonly referred to as perimetry, the sensitivity across the field of view of each eye of the test subject is mapped. Systems and methods of the present application achieve this goal by presenting stimulus of controllable intensity at individual field angles using one or more light field displays and recording the response of the subject to each of these 'questions.' The diagrams provide more detail on how the near eye light field display creates a stimulus and how it simulates focus. The term 'field angle' should be considered as the location (in visual field angle) of a pixel which can be used to form a portion of a stimulus image which typically has an illuminated region covering a range of field angles.

Figures 2, 2A, 2B, 2C:
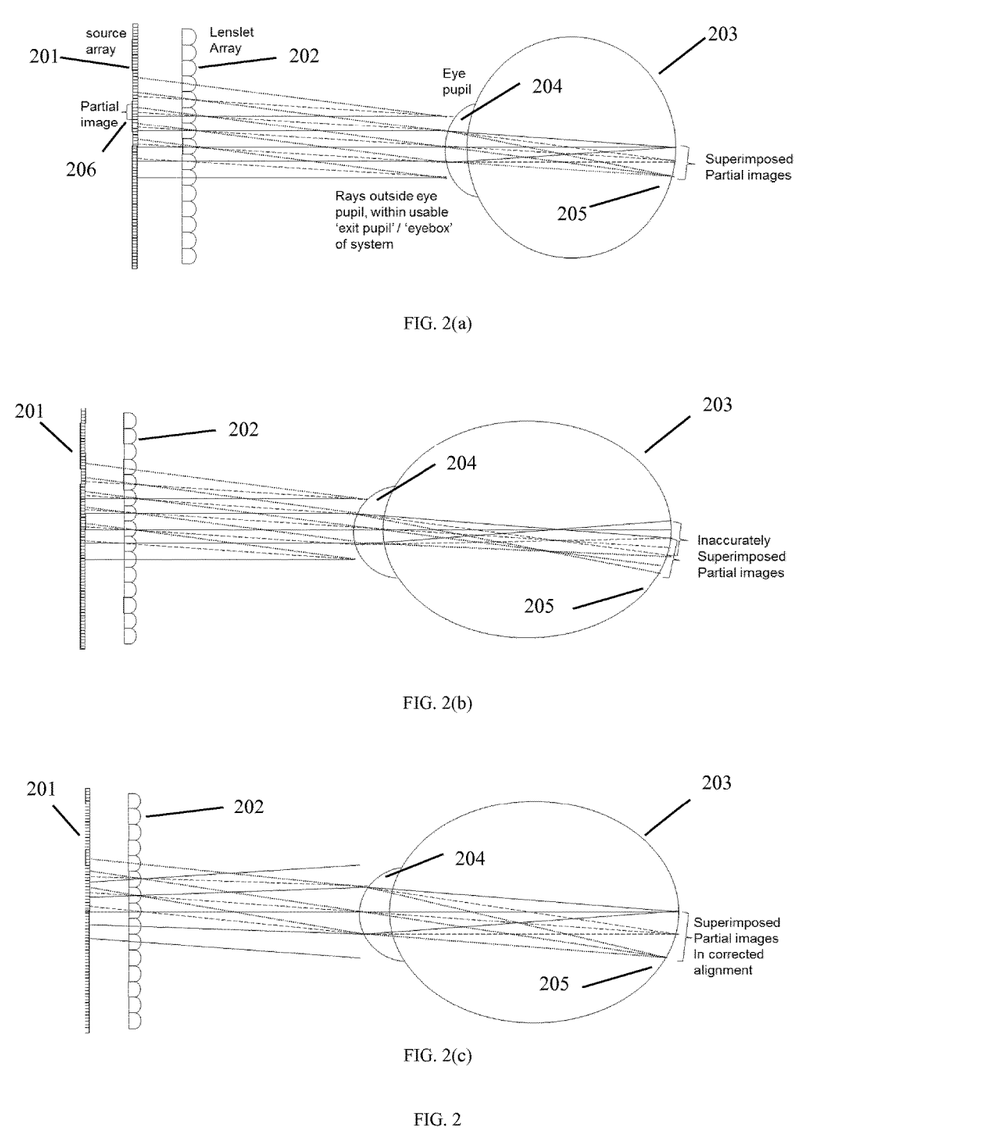
FIG. 2 illustrates the use of light field displays to perform visual field testing.
FIG. 2(a) illustrates an embodiment of a light field display visual field testing system for an emmetropic eye.
FIG. 2(b) illustrates when the imaging configuration of FIG. 2(a) is applied to a myopic eye.
FIG. 2(c) illustrates a light field display visual field testing system applied to a myopic eye accounting for the refractive condition.

FIG. 2(a) illustrates one embodiment of a light field display visual testing system. A light field display is constructed from a high density active source array 201, such as an organic light-emitting diode (OLED) pixel array, at the back focal plane of a passive beam steering array, in this case a lenslet array 202. The intensity of individual pixels in the source array is controlled to create the light field. Each element in the source corresponds to a unique ray within the light field. In the figure, rays are illustrated for three different field angles (in a plane capturing the direction of propagation), illustrated in different linestyles (dashed, dark and light). Only rays originating at the center of a source display pixel and passing through the center of a lenslet are illustrated, as these closely approximate the small beam generated by each pixel and collimated by each lenslet, and are sufficient to describe the light field in terms of the position and angle in a particular plane L(u,v,s,t) of each individually controllable channel of light. The source pixels are located at the focal point of the lenslet array, conjugate to the retina. To illustrate the ray paths, the embodiments in FIG. 2 show a large separation between the active source array and the passive beam steering array. These two elements could actually be positioned in close proximity or be mounted together as a single entity as shown in the other figures. The term light field display as used herein refers to the combination of an active source array and a passive beam steering array.

The light field display is placed near the eye 203 of the test subject, at a distance much shorter than the ability of most persons to focus comfortably, however at a comfortable eye relief A desirable separation between the display and eye is less than 5 cm. The rays start at the light producing source array and terminate at the eye. Rays which pass through the pupil 204 of the eye are illustrated terminating at the light sensitive retina 205 at the back of the eye. Rays which are blocked by the pupil of the eye are illustrated terminating at the anterior portion of the eye. For each lenslet there is a small region of the source array which illuminates the pupil of the eye which provides the useful light for creating a stimulus. This region corresponds closely with an area of the source we describe as a partial image 206. The partial image describes a small part of the complete field of view containing the stimulus. Within this partial image, adjacent pixels on the source array illuminate adjacent locations on the retina. For an ideally aligned eye, the ray passing through the center of the pupil originates at the center of the partial image. Rays originating from the edges of each partial image may be occluded or vignetted by the pupil of the eye (depending on the alignment of the pupil to the display) and do not add to the intensity of the stimulus on the retina. Adjacent partial images have a significant degree of overlap in the field angles contained, however there is a progression such that more extreme field angles are included and less extreme field angles are excluded as we consider lenslets that lie farther from the center of the field of view. A region of dark pixels on the source array surrounds most partial images and aids in alignment tolerances of the pupil of the eye to the array.

The image forming apparatus of the eye causes parallel rays to be bent to converge at the focal point of the eye. For the individual with emmetropic vision as shown in FIG. 2(a), needing no refractive correction, this focal point lies at the light sensitive retina at the back of the eye. In this case, a stimulus which appears to come from an infinite distance appears to the test subject to be in sharp focus. The light field display simulates this condition by illuminating a set of parallel rays from the same field angle. Such rays are created for a given field angle, by illuminating pixels on the source array which have the same offset from the axis of their respective lenslets. As illustrated in FIG. 2(a), the five solid lines corresponding to the on axis visual field originate at five pixels that are located at spacings on the source array equivalent to the lenslet array separation and are directly centered underneath their respective lenslets. The five dashed lines illustrate field position just slightly off axis, note that the spacing on the source array is still equivalent to the lenslet spacing, however the illuminated pixels are offset from the centers of their respective lenslets. The five dotted lines illustrate a more extreme field angle. Underneath some lenslets, all three field angles are included in the same partial image, however as we progress to more off center lenslets, the on axis field angles are omitted from the partial images, as more extreme angles (not drawn) are included. The three field angles drawn do not necessarily depict field angles associated with adjacent pixels on the source display. Depending on the density of the source array there could be many rays in the light field between the rays that have been illustrated here. Rays are bent by the optics of the eye and create a visual signal where they intersect the retina. The parallel rays corresponding to a single field angle converge at the retina and the power is additive. The position on the retina corresponding to a single field angle is being illuminated from different positions within the pupil and the stimulus intensity delivered at the retina is the sum of the signals transmitted through the pupil and incident on the same location on the retina.

The above text describes how individual rays of the light field, going through different locations of the pupil converge to create a single field angle pixel; it is also useful to consider how the partial images come together to create a total stimulus image. If we consider only a single lenslet and its partial image, it is straight forward to observe that the retina of the emmetropic eye is optically conjugate to the source display and the partial image is reproduced on the retina as an inverted and magnified copy of the small portion of the total stimulus image. If we now consider a neighboring lenslet and its partial image, it will also form an inverted, magnified copy on the retina. The portions of this neighboring partial image which contains the same field angles as the first partial image are coincident on the retina and do not introduce additional blurring of the image. The portion of this neighboring partial image that does not contain the same field angles as the first partial image extends to new regions of the total stimulus image and will overlap with the field angles of yet another partial image from the next neighboring lenslet.

Most of the population requires some refractive correction in order to see objects clearly. For myopes (i.e., nearsighted) the natural focal point lies considerably anterior to the retina, usually because the eye is physically longer than normal, although occasionally because the anterior surface of the eye (cornea) has a steeper surface curvature than normal. FIG. 2(b) illustrates the stimulus created for an emmetrope (FIG. 2(a)) applied to a myopic eye. Each partial image suffers minimal blur because of low numerical aperture (NA). The partial images are not coincident at the retina 205 causing blur in the superposition when viewed by a myope. To correct for this case, a stimulus which appears to come from a close distance in front of the eye would appear to the test subject in sharp focus. The light field display simulates this condition and can digitally correct for refractive errors by illuminating a set of diverging rays from the same field angle, effectively rendering a model of the stimulus as an object located at a comfortable viewing distance for the test subject from the perspective of each eye. The intersection point of these rays is the virtual location of the object. Such rays are created for a given field angle, by illuminating pixels on the source array which are nearer to each other than their respective lenslets. (Note that this creates an image that appears to be in focus at a comfortable working distance, which is different from 3D movies where binocular vision convergence between the two eyes is used to make objects appear to be at different distances without affecting the focus of the eye.) The refractive error of the patient could be entered by the doctor though a user interface on the device or could be stored in a reference database such as an electronic medical record (EMR) and communicated to the instrument over a network connection. The instrument would then adjust the rendering of the light field display based on the refractive correction of the patient to produce a stimuli that appears in focus.

FIG. 2(c) illustrates how the light field display can shift the off axis parallel images to make the partial images coincident at the retina depending on the refractive condition of the particular subject, in this case, a subject with myopia. The five solid lines corresponding to the on axis visual field originate at five pixels that are located as spacings on the source array just smaller than the lenslet array separation and only the central pixel is centered underneath its respective lenslet. In this way, the corresponding pixels in adjacent partial images move closer on the source display. The five dashed lines illustrate field angle just slightly off axis. Note that the spacing on the source array is still slightly smaller than the lenslet spacing. When rays are bent by the optics of the eye and create a visual signal where they intersect the retina, the divergent rays corresponding to a single field angle converge at the retina and the power is additive. When we consider the partial images, it is clear that each partial image is no longer strictly in focus at the retina, however because the NA of each illuminated path is small, the depth of focus is large, especially compared to the spatial information content of the stimulus. The correction applied to each partial image superimposes the very slightly defocused partial images and the resulting blur is within tolerance for the purposes of the exam. In addition to shifting the partial images relative to one another to remove blur, one can also change the size of the image to correct for magnification associated with myopia, or adjust the distortion to mimic the distortion created by a trial lens used to correct refractive error in a classic perimeter.

Hyperopes (i.e., far sighted) have a focal point that lies beyond the retina because they have a short eye or relatively flat cornea. Hyperopes are corrected by creating the opposite correction applied for myopes. The light field display simulates this condition by illuminating a set of diverging rays from the same field angle. Such rays are created for a given field angle, by illuminating pixels on the source array which are distant to each other compared to their respective lenslets, thus the corresponding pixels in adjacent partial images move farther apart on the source display.

The light field display can be used to correct higher order aberrations beyond focus. Astigmatism, or cylinder error, is the condition where the eye has different refractive power along orthogonal axes, usually caused by an anterior surface of the eye which has a toroidal surface figure rather than one which is rotationally symmetric. Astigmatism is described in terms of the cylindrical power of the lens used to correct the condition and the orientation of that lens. To correct for astigmatism, the distorting correction described for myopia or hyperopia is applied, on the axis where the astigmatic correction is needed, rather than rotationally symmetrically. Corrections for spherical power and astigmatism can be applied simultaneously by applying asymmetric distortions to the rendered data.

A key tradeoff in light field displays is a sacrifice of projected imaging resolution for an ability to simulate a range of focus depths. As described by Lanman, the ability to simulate a focus adjustment increases as with a decrease in the lenslet focal length (Lanman et al "Near-eye light field displays"). As the ability to simulate focus increases, the potential spatial resolution for a given source array decreases. As the focal length of the lenslet decreases, the lenslet diameter, and field of view of each lenslet decreases, however the total field of view increases.

The above description can be related to standard light field descriptions. The light field visual stimulus can be described as Ls(u,v,s,t), which comprises a collection of views of the stimulus from different angles (s,t) with an intensity value at each of (u,v) positions within a plane. The portion of the stimulus which passes through the pupil of the eye is physically propagated through the optics of the eye to create a pattern of intensity on the retina Ir(u,v). When the eye is emmetropic, the resulting corrected Ir(u,v) appears to the patient to be 'in focus' and is functionally equivalent to a standard intensity pattern for the purposes of the exam. The rendering of the stimulus may be adjusted to compensate for the patient refractive error including focus error and cylinder error to create a field Ls(u,v,s,t)'. The resulting corrected Ir(u,v)' appears to the patient, with refractive error, to be 'in focus' and is functionally equivalent to a standard intensity pattern with an additional corrective lens for the purposes of the exam.

The light field illumination Ls(u,v,s,t) may be created by a display consisting of a high density active source array and a beam steering array. The active source array, such as an OLED pixel array consists of many switchable sources in a positional grid. The passive beam steering array exists to direct beamlets, originating from sources, into defined directions. The passive beam steering array may consist of a lenslet array where the sources are located at the back focal plane. Each lenslet of the steering array is illuminated by a portion of the pixel array which forms a partial image corresponding to a portion of the full field of view.

One method to calculate the appropriate stimulus description at the light source array is to use the principle of light path reversibility, and model the elements of the system in a ray path simulator. In this case, one back propagates rays from an image of the ideal stimulus on the retina through a model eye with a restricting mask at the size and location of the pupil eyebox (or more accurately, the size and location of the real pupil of the eye, if known), and through the lenslet array in front of the light source array. The intensity at which rays strike pixels is proportional to the intensity which the pixels should be driven to achieve the desired stimulus. Compensation of refractive error may be achieved by adjusting the eye model to have refractive error similar to the patient. Alternatively, the compensation for focus error is equivalent to the rendering of the object at a different depth, which is equivalent to the rendering of the object as propagated through a spherically shaped refractive boundary acting as a lens. The rendering of cylinder error is equivalent to the rendering through a cylindrically shaped refractive boundary. Correction of refraction includes translations, magnifications, or distortions of partial images on the active source display.

Figure 3:
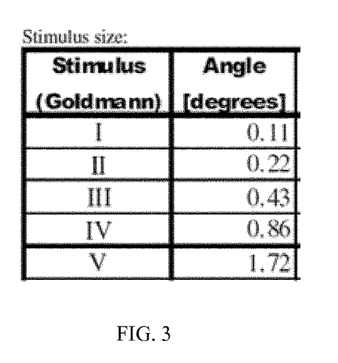
FIG. 3 is a table showing the standard (Goldmann) stimulus sizes used in standard automated perimetry.
Figure 4:
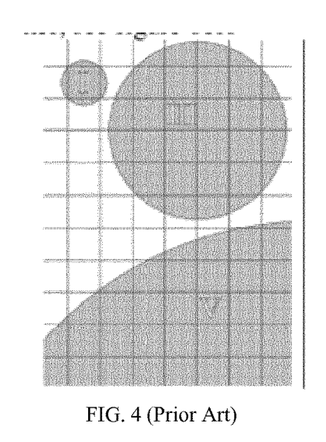
FIG. 4 illustrates the Goldman stimuli I, III, IV as they would be digitally created on an industry standard XGA display.

Here we recognize a particular synergy with the technology of light field display with the application of visual field testing, in particular standard automated perimetry. The size characteristics of traditional visual field stimuli (Goldman standard) are shown in FIG. 3. The most commonly test used is the stimulus size III and larger, whereas the smaller stimulus size I is rarely used. Testing over the central +/−30 degrees (central visual field) provides most information required for clinical decisions, however the ability to do wider field tests remain widely desired by clinicians. The Goldman size III stimulus is circle with a visual field angle diameter of 0.43 degrees. When the stimulus is classically projected onto the surface of a bowl at a 300 mm distance from the eye, it has a diameter on the projection screen of 0.58 mm. FIG. 4 describes the Goldman stimuli I, III, and V as they would be digitally created on an industry standard XGA display. On this display, the size I stimulus is represented by approximately one pixel while the size III stimulus is represented by approximately four pixels across its diameter. Assuming a single pixel width should correspond to the visual field diameter of the stimulus, the size III stimulus requires approximately 256×192 effective pixels to display with sufficient resolution over a 60 degree field of view. It would be desirable to optimize the light field display to maximize the field of view and potential refractive error correction while maintaining sufficient resolution to represent a Goldman size III stimulus. Comparison with the equations in Lanman suggests that such a resolution and field of view can be achieved with the same OLED source array used in the light field display demonstrator (15.36 mm×8.64 mm; 1280×720 pixels) if the working distance is reduced to 10 mm with a lenslet array focal length of approximately 2.5 mm A 14 mm working distance can be maintained with a 35% increase in the lateral dimension of the array, the same pixel pitch, and the same focal length lenslet array. Such a stimulus would be compatible with current protocols for threshold static automated perimetry. An extension to Goldman kinetic perimetry requires a somewhat larger field of view, but similar lateral resolution.

In order to locate defects in vision according to retinal coordinates, it is useful to maintain the subjects gaze in a particular direction during testing. Just as stimulus questions can be presented to a patient by modulating the intensity of light at an arbitrary position in the field, so a fixation target can be presented to a patient using the light field display. The intensity of a fixation target may be brighter or darker than the surrounding field, and is usually located close to the center of the field. The same methods of correcting for refractive error for the stimulus apply to the fixation target, allowing the patient to see this location in clear focus. The fixation should be clearly distinct from the stimuli questions. Usually the fixation has a distinctive shape or is presented with a constant intensity whereas the stimuli questions have a different spatial extent and are present only briefly.

A noted problem in simulating the stimuli currently possible with bowl perimeters is the extremely high dynamic range required to test the range of individuals covering individuals with normal vision and individuals who are nearly blind in some visual fields. Current testing devices have a range of 52 logarithmically spaced ranges from 0 dB corresponding to 10,000 apostilbs to −51 dB corresponding to 0.08 apostilbs. Digital drivers in standard display technology are typically limited to a maximum 8 bit resolution per pixel on a linear scale. While methods have been proposed to overcome these limitations (see for example U.S. Pat. No. 8,132,916), these come with complexity. Because the light field technique inherently attempts to superimpose multiple pixels, the effective bit depth increases with the number of superimposed pixels. To achieve fractional bit depth, corresponding pixels in neighboring partial images may be set to values differing by a least significant bit. If for instance 9 lenslets illuminate the pupil for a particular field, the dynamic range of the correctly 'focused' display is increased by a factor of 9. This is approximately analogous to 'dithering' used in traditional displays to achieve color palettes not addressable by the resolution of the display, however in this case the pixels are literally superimposed on the same portion of the retina rather than being in close proximity and approximately fused by the visual system.

Binocular or monocular testing can be straightforwardly implemented by presenting stimulus in only the display located in front of the eye to be tested. For monocular testing, the binocular nature of this device could improve fixation by providing a fixation target in both eyes. Likewise, background illumination may be optionally presented to the unstimulated eye in monocular testing.

Modern bowl perimeters include an eye tracker to gage the position of presented stimulus relative to the gaze direction of view of the individual, as well as to ensure that the subject's eye is laterally aligned correctly to the device (see for example U.S. Pat. Nos. 5,220,361 and 8,684,529). A similar gaze tracking camera could be incorporated into the light field display visual field testing system. A stimulus may be delayed until the subject's eye returns to a correct alignment, a stimulus position may be adjusted to conform to the current position of the eye and maintain an intended area of retinal simulation, or the actual alignment of the eye when the stimulus was delivered can be used to adjust the test results to show the stimulus in the position where it was actually delivered. An image of the eye observed by the administrator of the exam also allows the administrator to give feedback if the subject appears to be losing attention or drifting to sleep. Lanman suggests that eye trackers inside the head mounted display would help provide inputs to the rendering of the light field and would allow a higher (resolution*field of view) product by tightening the tolerance on the 'eyebox' (the location where the human pupil must be located to create an artifact free rendering), and allowing more efficient use of the source display area with a smaller 'dead zone' around each partial image.

Figure 5:
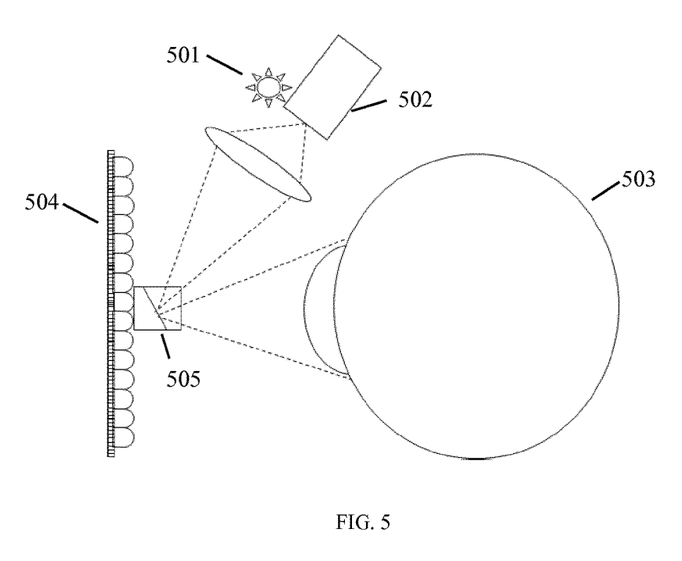
FIG. 5 illustrates how a gaze tracking camera could be combined with a light field display visual field testing system.

Gaze trackers may be implemented by including cameras aimed at the test subject's eyes as illustrated in FIG. 5. An infrared illuminator 501, also directed towards the subject's eye 503, is matched to the transmission band of an eye tracking camera 502. In this way the eye tracking camera is not sensitive to the illumination of the light field display 504 which create primarily visible light. The eye tracking camera uses the image of the pupil and iris, as well as the reflexes of the illuminator from specular surfaces of the anterior eye to determine the direction of gaze as well as the location of the pupil relative to the display units. The light field can be optimized to the position of the patient's pupil to reduce or prevent artifacts in the testing. The illumination and camera may be placed just outside the field of view of the displays or may be coupled in to a more central location. It is frequently advantageous to place the eye tracking camera at an angle close to the gaze axis. This may be achieved by placing a small reflective surface 505 in front of the display where the camera may be coupled in. Because the camera is operated at a different set of optical frequencies than the display, a dichromatic mirror can effectively superimpose the line of sight of the camera and the underlying stimulus. For simplicity, it may be advantageous to directly affix a reflective element to the array or form a reflective facet out of small region of the lens array. This occludes a small part of the visual field. This camera may also be used for pupilometry and eye motion and related analysis. It is possible to ask questions over portions of the visual field which may be occluded by such structures by temporarily adjusting the location of the fixation target, such that the relative visual field moves over an area of the display that is capable of presenting a stimulus.

Multiple panels of the light field displays may be attached consecutively to each other to provide a wider field of view similar to the concept presented in U.S. Pat. No. 6,529,331. For the application of perimetry, where the subject is typically asked to look directly ahead at a central fixation point, these side view panels may have a lower degree of spatial resolution than the central field of view. The use of multiple adjacent displays where the side displays have a lower spatial resolution than the central field displays is an optically simple way to create foveation—the effect where high spatial resolution display is presented primarily to the central field of view where the eye has maximum capability for high resolution. Lower spatial resolution side mounted displays may utilize larger source displays, with less pixel density, or may be identical to the central source display, however placed closer to the eye.

Figures 6, 6A, 6B:
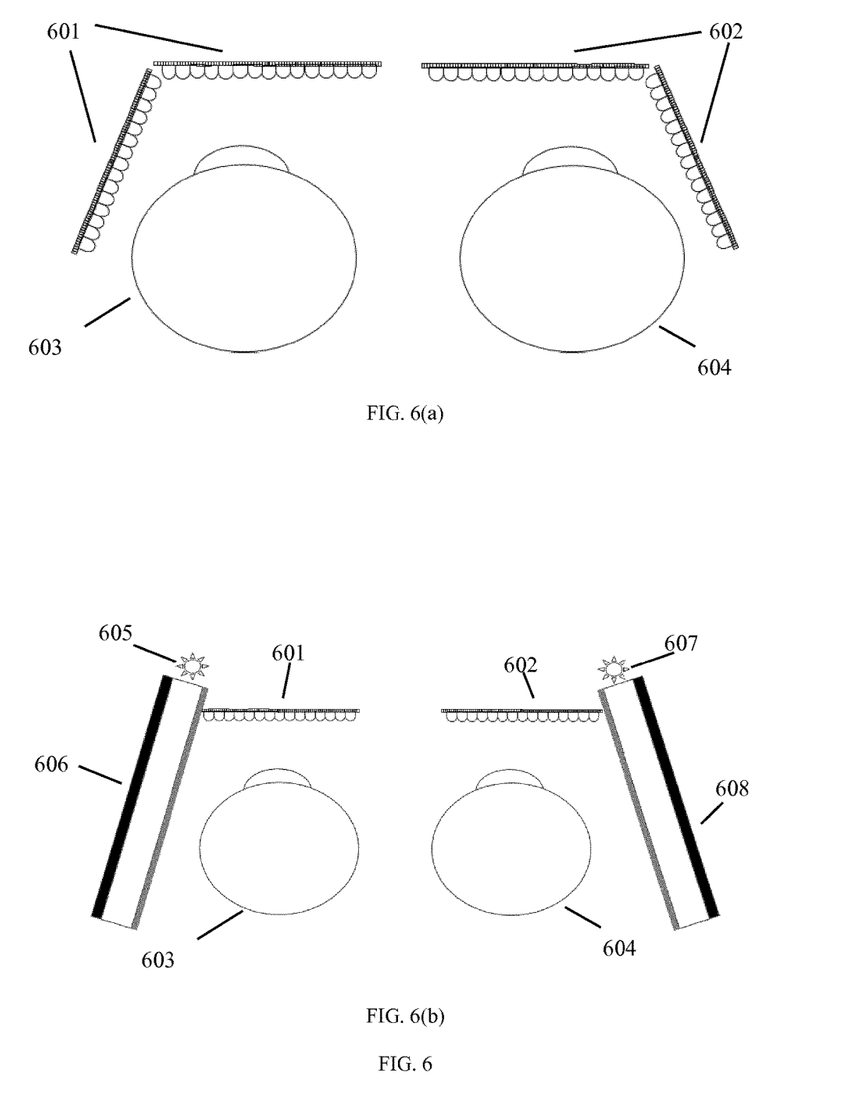
FIG. 6 illustrates two embodiments of wrap around light field visual field testing systems.
FIG. 6(a) illustrates an embodiment using a plurality of light field displays for each eye.
FIG. 6(b) illustrates an embodiment in which a non-stimulus providing wrap around material is used in addition to a single light field display for each eye.

Wraparound, peripheral light field panels help provide an important feature of a visual field analyzer—the ability to precisely control the illumination, not only of the stimulus and central field, but of the periphery (perceptible region outside the central visual field) and essentially all light entering the eye. It is important to control this illumination because the eye self-adjusts its sensitivity according to its environment, both by pupil dilation and by attenuation of the photoreceptors and neural circuitry. When the instrument adequately provides its own isolation, test results are relatively independent of the room in which the individual takes the test. Areas of the perimeter which may not be stimulated may still be actively illuminated to create an environment closely approximating the bowl perimeter. One example of wrap around light field panels for use in a visual field testing device is illustrated in FIG. 6(a). Here two light field display panels 601 are used for testing left eye 603 and two light field display panels 602 are used to test right eye 604. Because the human eye has high resolution only near the central field of view, the light field display on the side illuminating the peripheral visual field could provide a lower angular resolution than the central light field display and/or the peripheral light field display can be placed closer to the eye than the central light field display. Alternatively as illustrated in FIG. 6(b), wrap around materials may provide approximately homogenous peripheral illumination control without the ability to provide localized stimulus. In one such embodiment, a shroud or side panels 606 and 608 may be manufactured from a transparent plastic with a frosted surface acting as a light pipe to uniformly distribute light from LEDs 605 and 607 while the stimulus presentation is accomplished from light field displays 601 and 602 for left and right eyes 603 and 604. The LED provides uniform and controllable illumination. The intensity and the color of this illumination can be adjusted for different tests. An opaque surface coating applied to the outside of the light piping, wrap around materials isolates the transparent material from the outside lighting conditions. The inner coating and material and geometric shape of the light pipe are optimized to provide uniform illumination. OLED or other luminescent materials can likewise cover the interior surface of a shroud blocking ambient room light. The wrap around visual concept can be extended to other environmental factors which may affect the concentration of the test subject. In particular it is advantageous to isolate the hearing of the individual taking the exam such that they are less distracted by events taking place in the room around them.

Figures 7, 7A, 7D:
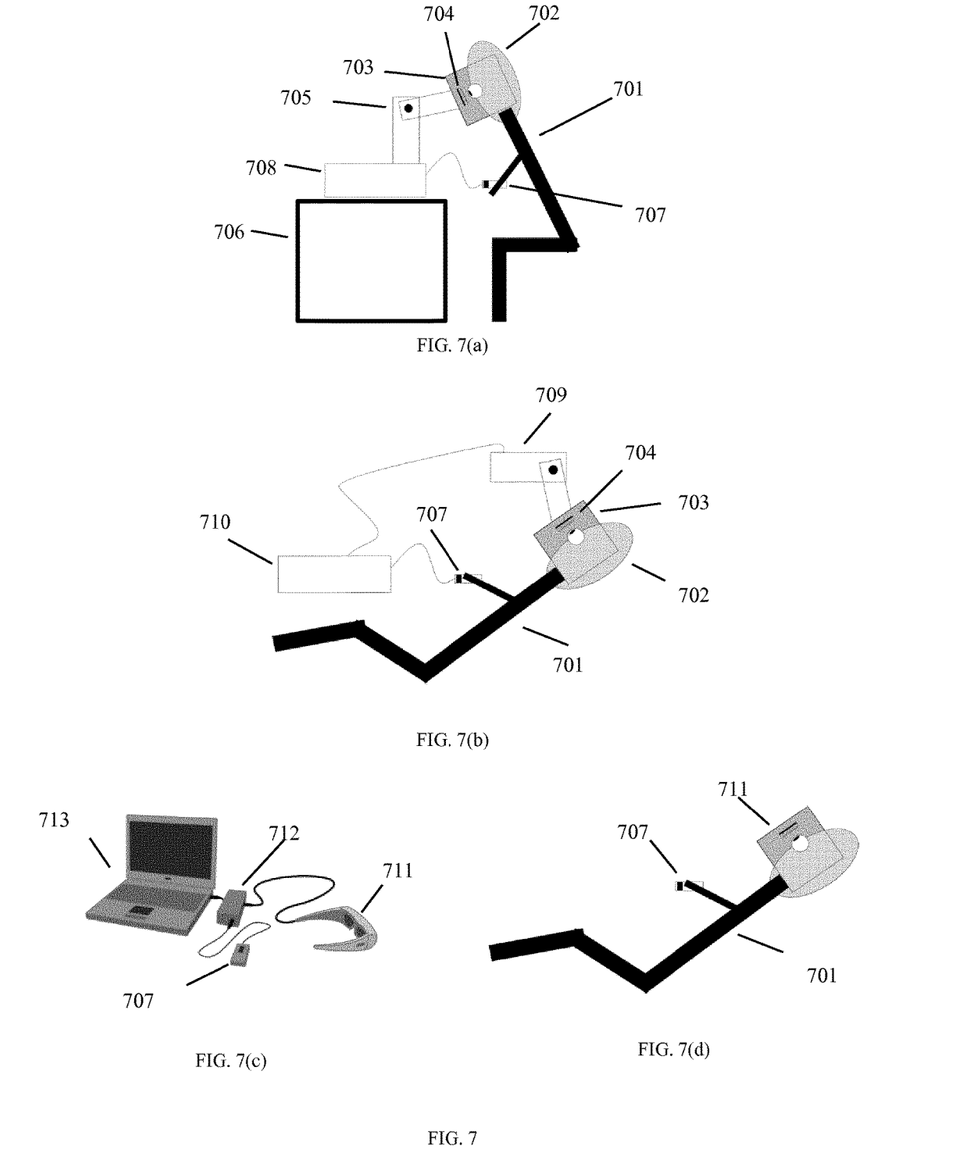
FIG. 7 illustrates several possible form factors for light field display visual field testing systems.
FIG. 7(a) illustrates a desk top embodiment.
FIG. 7(d) illustrates one use scenario for the head mounted embodiment of FIG. 7(c).

The much smaller form factor of the near eye light field display enables a compact device that is functionally analogous to the bowl perimeter. By making the display technology smaller, new form factors and workflows are enabled. In the simplest modification, the desktop footprint of the device can be significantly reduced compared to an HFA type device as illustrated in FIG. 7(a). Here a seated patient 701 leans into rest their face 702 on an interface structure 703 that includes the light field display 704. The interface structure is mounted to a support structure 705 that allows the interface structure to be adjusted relative to the patient. Such a configuration better conforms to the subject's natural posture. The patient depresses a push button 707 to indicate that they perceived the stimuli. The system sits on top of a table or cart 706 and is operably connected to a processor for receiving and processing the test results and display for displaying the results. The processing and displaying functions could be contained within the instrument 708 or be connected via a network connection (e.g. wireless or LAN). The display could be done on a general multi-use computer workstation at a clinician's desk.

An alternative form factor for a light field display visual field testing system is illustrated in FIG. 7(*b*). In this case, the light field display 704 and interface structure 703 may be mounted on an arm 709 and positioned near the head 702 of the test subject 701 while he or she sits in a comfortable position, for example in an exam chair or wheelchair. The display and interface are operably connected to the rest of the system 710 which receives response data from the patient via a push button interface 707.

FIG. 7(*c*) illustrates a head mounted or goggle type form factor for the light field display visual field testing system. Here the light field displays would be mounted inside a pair of glasses 711 that is operably connected to an electronics interface 712, an operator interface 713, in this case a laptop computer, and a handheld feedback device 707. While the embodiment pictured in FIG. 7(*c*) shows wired connections, one skilled in the art would appreciate that wireless connections such as bluetooth or wife could also be used for transmission of data and connection. A lightweight head mounted embodiment can be brought to the subject wherever that person is, and does not require moving the person. FIG. 7(*d*) illustrates one use scenario of the head mounted embodiment where the subject 701 is in a reclined position while wearing the head mounted display 711 and holding the feedback device 707. This arrangement could be particularly advantageous for testing patients in the hospital setting.

Figure 8:
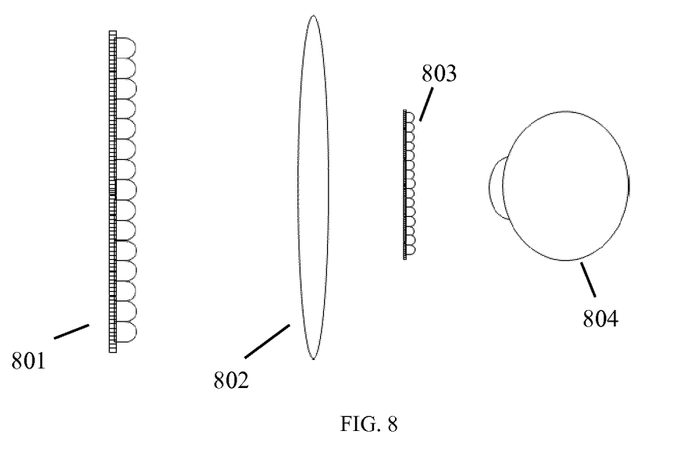
FIG. 8 illustrates use of a relay system to re-image a light field display in a visual field testing system.

The advantages of pure digital refractive correction for perimetry using a light field display are valuable independent of the small form factor enabled by the near eye display concept. FIG. 8 shows how a light field display may be reimaged in front of the eye from another plane by refractive optics. The light field display 801 is imaged by a lens or lens system 802 to appear as an image 803 in close proximity to the eye 804. In this case the light field display, in terms of the high density source array, and lenslet beam steering array, is similar to the prior embodiments, however specifications such as pixel density may be relaxed because the refractive optics may present a demagnified view of the original light field display. Additionally constraints on eye relief may be reduced because the location of the image of the display presented to the eye may be far from any physical optic and can comfortably be placed very near the eye without risk of contact.

It is intended for the visual field analyzer to isolate the test results from environmental factors in the room where the individual takes the exam. On the other hand, clinical workflow, and the comfort of the test subject may require relief from the isolation which is best served without extracting the subject from the test environment. The light field display could be used to present visual information other than the examination to the subject. A 'Video See Through' function which uses an externally facing camera and live rendering of the outside world onto the visual field of the subject could be introduced to enhance communication with the test operator. Likewise, a 'Microphone Hear Through' function would enhance the ability to verbally communicate with a subject whose hearing is isolated from the room environment. Video See Through and Microphone Hear Through features may be optimized and adjusted for the particular disabilities (e.g. hearing impairments, visual impairments) of the subject tested, therefore actually enhancing the communication with an operator. Audible instruction may be further enhanced by making the language selectable, overcoming another key communication barrier. The Video See Through and Audio Hear Through functions can easily be virtualized, allowing remote communication, or instructions delivered by a lifelike virtual assistant. A virtual assistant may describe to the subject how to take the exam or may provide coaching instructions during the exam. Coaching during the exam is frequently required when the subject appears to be losing concentration or eye fixation during a long exam. Virtual assistance may help reduce the variability in exam results caused by different operators. Such remote or virtual assistance is particularly valuable if the device is used outside the ophthalmic care environment, such as at remote clinic, doctors office or at the subjects home. A video showing the test process, or a preview of presented stimuli that are not part of the exam, helps orient the test subject immediately upon viewing the device.

The classic feedback collection system is a simple, handheld controller tethered to the device by a wire transmitting an electrical impulse when the test subject presses a solitary button in response to having perceived a stimulus. This classic arrangement has proven very effective, in particular with elderly subjects with a limited ability to perform complex tasks. The shape of the controller is easy to hold in one hand, but is simultaneously easy to rest on a flat surface for subjects who cannot hold the object for the duration of the test. The wired tether is useful because it provides an easy means to recover the controller if it is dropped, and the wired remote is very difficult to lose. On the other hand, the wired remote lacks flexibility. A wireless remote allows a flexible pairing of different types of controllers for subjects with different abilities, as interfaces evolve, or as the preference of users changes over time. More complex controllers, for example a controller that allows the test subject to indicate, not only that a stimulus was seen, but the quadrant of the visual field in which the stimulus was seen. Such feedback may provide useful confidence measures, but may also be too complex for some subjects.

Voice sensitivity can add multiple functionalities to the perimeter. A voice activated stimulus response such as an external microphone can enhance the compactness of the device by removing the need for a hand controller. Second, by analysis of the voice properties for each response, the test may assign confidence scores on the responses, essentially analogous to a telephonic lie detector (see for example U.S. Pat. No. 3,855,417). As is commonly observed in day to day life, the confidence of a person in responding to a question is reflected in the timing and tone of voice. Of course this response varies greatly between individuals. In general the method of calibrating a confidence measure is to present the subject with strong stimuli that are confidently observed, non-existent stimuli that if observed represent a false positive, and intermediate stimuli that may be observed with less confidence. The timing of the response relative to the timing is a characteristic already investigated for visual field analysis response confidence rating with the handheld controller. Because the vocal signal is more information rich than a button press, more detail can be extracted from it. Factors such as timing and tonality may be determined from a wavelet analysis of the vocal response. Vocal confidence calibration testing can be distributed throughout the exam as is currently performed with false positive and false negative rate testing in current testing strategies. In addition, voice sensitivity adds an intuitive means to communicate with a remote or virtual test operator.

Any one of a number of functional visual testing strategies can be performed with a light field display visual field tester as described herein. A test strategy typically contains a series of predefined stimulus sizes, intensities, and test locations. The flexibility of light field displays would allow for adaptable rendering based on the responses of the patient. In addition, with predicted increases in source display resolution, the (resolution*field of view) product increases, allowing a near eye light field device with visual field analysis capability to perform or be combined with multiple vision testing functions. These functions may include:

Visual field analysis utilizing frequency doubling stimulus

Confrontation fields generalized visual acuity testing using an equivalent to the Snellen chart.

Stereopsis examination

Color vision testing

Digital phoropter (subjective testing of refractive error and correction)

Although various embodiments that incorporate the teachings of the present invention have been shown and described in detail herein, those skilled in the art can readily devise many other varied embodiments that still incorporate these teachings.

The following references are hereby incorporated by reference:

PATENT DOCUMENTS

U.S. Pat. No. 5,323,194
U.S. Pat. No. 5,220,361
U.S. Pat. No. 8,684,529
U.S. Pat. No. 8,668,338
U.S. Pat. No. 5,737,060
U.S. Pat. No. 5,864,384
U.S. Pat. No. 5,880,812
U.S. Pat. No. 7,936,392
U.S. Pat. No. 8,132,916
U.S. Pat. No. 6,529,331
U.S. Pat. No. 3,855,417
U.S. Pat. No. 6,386,706
Non-Patent Literature
R. Ng, "Digital light field photography" 2006 Thesis
Lumsdaine et al. "The Focused Plenoptic Camera", ICCP April 2009
Lanman et al "Near-Eye Light Field Displays" in ACM SIGGRAPH 2013 Emerging Technologies, July 2013

The invention claimed is:

1. A method for testing the visual sensitivity of an eye of a subject, comprising:
    displaying a plurality of visual stimuli to different locations of the eye of the subject, said stimuli generated using a light field display, wherein the light field display corrects for the refractive error of the subject's eye when generating the visual stimuli;
    recording the response of the subject to the stimuli;
    processing the responses to determine the subject's visual sensitivity at different locations in the eye.

2. A method as recited in claim 1, wherein the refractive error is focus.

3. A method as recited in claim 1, where the refractive error is spherical or cylindrical.

4. A method as recited in claim 1, wherein the stimuli are part of a standard automated perimetry test.

5. A method as recited in claim 1, further comprising performing a second type of vision testing using the light field display.

6. A method as recited in claim 1, wherein the stimuli are displayed in the central field of vision of the subject and further comprising controlling the illumination in the periphery.

7. A methods as recited in claim 6, wherein the illumination in the periphery is controlled using a second light field display or a non-stimulus producing homogenous illumination control.

8. A method as recited in claim 1, further comprising recording an image of the subject's eye during the test and using the images to do one of: adjust the position of a stimulus, delay the presentation of a stimulus, or adjust the test results.

9. A method as recited in claim 1, further comprising presenting auditory information to the subject during the test.

10. A method as recited in claim 1, wherein the response of the subject is recorded using a button click or a microphone.

11. A method as recited in claim 1, wherein the displaying, recording and processing steps are carried out on both eyes in a binocular arrangement.

12. A device for testing the visual sensitivity of an eye of a subject comprising:
    a light field display for generating a plurality of visual stimuli presented to different locations of the eye of the subject wherein the light field display corrects for the refractive error of the subject's eye when generating the visual stimuli;
    a feedback collection detector for recording the response of the subject to the stimuli presentations; and
    a processor for analyzing the responses from the feedback collection detector to map the visual sensitivity of the subject at different locations in the eye.

13. A device as recited in claim 12, wherein the light field display comprises an active source display coupled to a passive beam steering array.

14. A device as recited in claim 13, wherein the active source display is an organic light emitting diode (OLED) array.

15. A device as recited in claim 13, wherein the passive beam steering array is a lenslet array.

16. A devices as recited in claim 12, further comprising an imaging system for recording images of the subject's eye during the testing.

17. A device as recited in claim 12, wherein the device is mounted to the subject's head.

18. A device as recited in claim 12, wherein the device is mounted to an adjustable arm for positioning relative to the subject's eye.

19. A device as recited in claim 12, wherein the visual stimuli are presented to the central region of the subject's field of view.

20. A device as recited in claim 19, further comprising a second light field display for controlling the illumination in the periphery of the visual field during the testing.

21. A device as recited in claim 19, further comprising a light pipe for controlling the illumination in the periphery of the visual field during the testing.

22. A device as recited in claim 12, further comprising a second light field display for generating a plurality of visual stimuli presented to different locations on the second eye of the subject in a binocular arrangement.

* * * * *

UNITED STATES PATENT AND TRADEMARK OFFICE
CERTIFICATE OF CORRECTION

PATENT NO. : 9,895,057 B2  
APPLICATION NO. : 15/120063  
DATED : February 20, 2018  
INVENTOR(S) : Alexandre R. Tumlinson Page 1 of 1

It is certified that error appears in the above-identified patent and that said Letters Patent is hereby corrected as shown below:

In the Specification

In Column 1, Line 50, after "reference)" insert -- . --.

In Column 4, Line 52, after "luminance" insert -- . --.

In Column 6, Line 15, after "relief" insert -- . --.

In Column 10, Line 15, after "2.5 mm" insert -- . --.

In Column 11, Line 53, delete "pupilometry" and insert -- pupillometry --, therefor.

In Column 13, Line 26, delete "wife" and insert -- wifi --, therefor.

In the Claims

In Column 16, Line 10, in Claim 7, delete "methods" and insert -- method --, therefor.

In Column 16, Line 49, in Claim 16, delete "devices" and insert -- device --, therefor.

Signed and Sealed this  
Twenty-sixth Day of June, 2018

Andrei Iancu  
*Director of the United States Patent and Trademark Office*